United States Patent [19]

Curtius et al.

[11] Patent Number: 4,774,244

[45] Date of Patent: Sep. 27, 1988

[54] USE OF PTERIN DERIVATIVES

[75] Inventors: Hans-Christoph Curtius, Zollikon, Switzerland; Heinrich-Georg Müldner, Weinheim, Fed. Rep. of Germany; Alois Niederwieser, Pfaffhausen, Switzerland

[73] Assignee: Kanagafuchi Chemical Industry Company, Limited, Kitaku, Japan

[21] Appl. No.: 149,118

[22] Filed: Jan. 27, 1988

Related U.S. Application Data

[60] Division of Ser. No. 18,789, Feb. 20, 1987, which is a continuation of Ser. No. 775,162, Sep. 12, 1985, abandoned, which is a continuation of Ser. No. 471,287, Mar. 2, 1983, abandoned.

[30] Foreign Application Priority Data

Mar. 3, 1982 [CH] Switzerland ............... 1300/82

[51] Int. Cl.$^4$ ............... A61K 31/50; A61K 31/495
[52] U.S. Cl. ............... 514/249
[58] Field of Search ............... 514/249

*Primary Examiner*—Stanley J. Friedman
*Attorney, Agent, or Firm*—Ladas & Parry

[57] ABSTRACT

L-erythro-5,6,7,8-tetrahydrobiopterin, L-sepiapterin, 1',2'-diacetyl-5,6,7,8-tetrahydrobiopterin and 6-methyl-5,6,7,8-tetrahydropterin can be used for the therapeutic treatment of patients with Parkinson's disease and of patients with depression.

1 Claim, No Drawings

USE OF PTERIN DERIVATIVES

This is a divisional of co-pending application Ser. No. 018,789 filed on Feb. 20, 1987 which is a continuation of application Ser. No. 775,162 filed Sept. 12, 1985 (now abandoned), which in turn is a continuation of application Ser. No. 471,287 filed Mar. 2, 1983 (now abandoned).

It was known that L-erytho-5,6,7,8-tetrahydrobiopterin is the natural cofactor of phenylalanine 4-hydroxylase (EC 1.14.16.1), tyrosine 3-hydroxylase (EC 1.14.16.2) and tryptophane 5-hydroxylase (EC 1.14.16.4) [Massey V., Hemmerich P. in The Enzymes (Editor: Boyer PD), 3rd edition, volume 12, pages 191–252, Academic Press. Inc., New York 1975]. The latter two are the key enzymes for the biosynthesis of the neuro transmitters dopamine and serotonin.

It has now been found, surprisingly, that L-erythro-5,6,7,8-tetrahydrobiopterin (abbreviated to BH$_4$ in the following text), sepiapterin, 1',2'-diacetyl-5,6,7,8-tetrahydrobiopterin and 6-methyl-5,6,7,8-tetrahydrobiopterin are effective for treating patients with Parkinson's Disease and patients with depression.

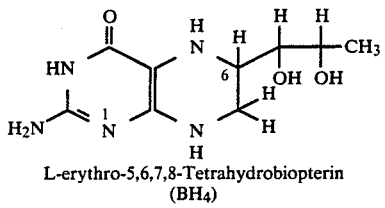
L-erythro-5,6,7,8-Tetrahydrobiopterin
(BH$_4$)

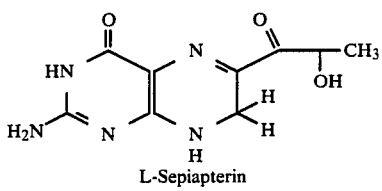
L-Sepiapterin

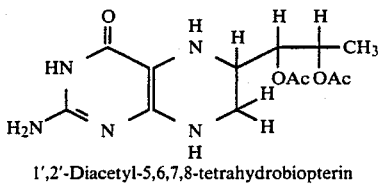
1',2'-Diacetyl-5,6,7,8-tetrahydrobiopterin

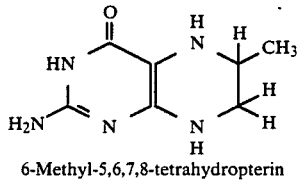
6-Methyl-5,6,7,8-tetrahydropterin

All patients with depression had previously been treated with commerically available antidepressants and, in some cases, also with various neuroleptic agents. Some of the patients had not responded to the medicaments administered; the clinical picture had remained unchanged. After oral administration of one gram of BH$_4$ (stabilized against oxidation by the addition of 100 mg of ascorbic acid) in orange juice, a prompt improvement in the clinical picture of severe depression occurred after about 4–5 hours.

Others of the patients had likewise previously been treated with antidepressants. These patients had responded positively to individual antidepressant medicaments, as is shown in wide clinical experience. As usual, the action had its onset in the period from one to three weeks. After discontinuation of this medication, the old condition recurred. In contrast to conventional antidepressant treatment, when BH$_4$ was then administered in the manner described above, a prompt improvement in the clinical state occurred within a few hours (4–5 hours).

No side effects were observed. The side effects which are customarily observed on initial administration of antidepressants and neuroleptics (of an autonomic and extrapyramidal nature) never occurred. After discontinuation of BH$_4$, the old clinical state recurred within 12 to 16 hours.

CASE DESCRIPTIONS

In the first place, the symptoms of endogenous depression of the inhibited depression type will be described:
1. Lack of motivation (lack of initiative to carry out mental tasks and motor actions with slowing down of movement and thought processes)
2. Lack of concentration
3. Affective apathy (inactivity, inability to feel grief)
4. Feelings of insufficiency, particularly in the morning
5. Severe loss of weight
6. Insomnia.

(1) Man aged 29 with endogenous depression (familial affliction), above symptoms 1 to 6 very pronounced, very severe loss of weight; a number of depressive phases which were not treated. Dissociative lapses and increased risk of suicide during the duration of the disease. Administration of BH$_4$ without previous antidepressant treatment; symptoms 1, 2 and 3 were virtually abolished or no longer detectable 4–5 hours later. No statement can be made about symptoms 4, 5 and 6, since their disappearance would only have been observed after a longer time.

(2) Man aged 43 with endogenous depression, mother a chronic depressive, symptoms as described in (1), also feelings of guilt. Hospitalized for 10 years and treated with antidepressants, but with inadequate success. Prompt improvement in the state in the form mentioned after administration of BH4.

The patients with Parkinson's disease who were investigated had previously been treated with L-dopa and bromocriptine mesilate (Parlodet, Pravidel) and partial compensation of the clinical picture had been achieved. The onset of action with this treatment was observed after about 6 days. Using BH$_4$, not only was the onset of action considerably more rapid but almost complete compensation of the existing complaints was achieved.

CASE DESCRIPTIONS

The three symptoms characteristic of Parkinson's disease are akinesia (slow and incomplete movements which give rise to the impression of a decreased motor initiative), tremor (which becomes less intense on movement or maintaining a position and more intense with emotional excitement) and depression (in the form of affective instability).

(1) Woman aged 72 with idopathic Parkinsonism (familial affliction) had the symptoms mentioned. The three groups of symptoms had virtually disappeared about 4–5 hours after oral administration of BH$_4$, and this is a result which had not been observed even after treatment with L-dopa.

(2) The same course was observed after treatment with BH₄ of a man aged 62 with idiopathic Parkinsonism.

The action was also demonstrated biochemically. For example, the concentrations of biopterin, dopamine and serotinin which are shown in Table 1 were found in the urine of two patients with an evident endogenous depression after administration of 1 g of tetrahydrobiopterin.2HCl(BH₄) or 0.9 g of diacetyltetrahydrobiopterin.2HCl.

TABLE 1

Biopterin, dopamine and serotonin in the urine of a patient with inhibited depression after oral administration of tetrahydrobiopterin or diacetyltetrahydrobiopterin respectively.

| Urine collection at time (hrs) | Concentration after 1 g of tetrahydrobiopterin.2 HCl | | | Concentration after D,9 g of 1',2'-diacetyltetrahydrobiopterin.2 HCl | | |
|---|---|---|---|---|---|---|
| | Biopterin mmol/mol Creatinin | Dopamin μmol/mol Creatinin | Serotonin | Biopterin mmol/mol Creatinin | Depamine μmol/mol Creatinin | Serotonin |
| 0 | 0.36 | 147 | 30 | 0.90 | 78 | 24 |
| 2 | 1.36 | 208 | 42 | 0.77 | 180 | 34 |
| 4 | 6.71 | 220 | 60 | 1.13 | 200 | 57 |
| 8-10 | 6.04 | 220 | 40 | — | — | — |
| 12 | 0.91 | 210 | 34 | 0.82 | 58 | 61 |
| Normal range | 0.31–1.09 | 70–170 | 22–60 | 0.31–1.09 | 70–170 | 22–60 |

The increase in the biopterin concentration in the urine shows that the administered tetrahydrobiopterin is at least partially absorbed and that the ester groups in the diacetate can be endogenously hydrolyzed. It is seen from the table that the initial figures for the two neurotransmitters were sometimes in the lower part of the normal range and that they increased under treatment with tetrahydrobiopterin or diacetyltetrahydrobiopterin. This was paralleled by the clinical improvement observed.

Treatment of patients with Parkinson's disease or with depression can start with an initial dose of the order of 1 g/day (about 15 mg/kg of body weight) and be continued, for example, with a dose of 500 mg (about 7.5 mg/kg) on the second day and of 200 mg/day (about 3 mg/kg) from the third day.

What is claimed is:

1. A method for the therapeutic treatment of patients with depression which comprises orally administering to the said patients an effective amount of L-erythro-5,6,7,8-tetrahydrobiopterin, L-sepiapterin, 1',2'-diacetyl-5,6,7,8-tetrahydrobiopterin or 6-methyl-5,6,7,8-tetrahydrobiopterin.

* * * * *